United States Patent
Napolez

(10) Patent No.: US 10,792,059 B2
(45) Date of Patent: Oct. 6, 2020

(54) NASAL EPISTAXIS CLAMP

(71) Applicant: Adolfo Napolez, Flossmoor, IL (US)

(72) Inventor: Adolfo Napolez, Flossmoor, IL (US)

( * ) Notice: Subject to any disclaimer, the term of this patent is extended or adjusted under 35 U.S.C. 154(b) by 126 days.

(21) Appl. No.: 15/877,728

(22) Filed: Jan. 23, 2018

(65) Prior Publication Data

US 2018/0206868 A1    Jul. 26, 2018

Related U.S. Application Data

(60) Provisional application No. 62/449,254, filed on Jan. 23, 2017.

(51) Int. Cl.
  *A61B 17/24* (2006.01)
  *A61B 17/122* (2006.01)
  *A61B 17/12* (2006.01)

(52) U.S. Cl.
  CPC .......... *A61B 17/24* (2013.01); *A61B 17/122* (2013.01); *A61B 2017/12004* (2013.01)

(58) Field of Classification Search
  CPC ....... A61B 17/08; A61B 17/24; A61B 17/122; A61B 17/2833; A61B 17/12104; A61B 2017/12004; A61B 2017/2825; Y10T 24/44983; Y10T 24/44991; A61F 2007/0006; A61F 13/126
  See application file for complete search history.

(56) References Cited

U.S. PATENT DOCUMENTS

| | | | | |
|---|---|---|---|---|
| 2,459,926 A | * | 1/1949 | Benedetto | A45D 8/20 132/277 |
| 5,383,891 A | * | 1/1995 | Walker | A61F 13/00063 206/438 |
| 5,899,918 A | * | 5/1999 | Knott | A61B 17/12 606/204 |
| 2009/0299405 A1 | * | 12/2009 | DeCrescenzo | A61B 17/12 606/201 |
| 2011/0088699 A1 | * | 4/2011 | Skipper | A61M 16/06 128/206.26 |

* cited by examiner

*Primary Examiner* — Tuan V Nguyen
(74) *Attorney, Agent, or Firm* — Jennifer S. Stachniak, Esq.; Johnson, Marcou, Isaacs & Nix, LLC

(57) ABSTRACT

The invention disclosed herein is a nasal epistaxis clamp. The present invention provides a nasal epistaxis clamp comprising a solid plastic surface at one end, having an external linear ribbed surface; and expandable limbs at the opposite end, wherein the medial surface of each limb comprises a plurality of bubbles. Also provided are methods and kits for using the nasal epistaxis device for treatment of nasal bleeding.

17 Claims, 2 Drawing Sheets

NASAL EPISTAXIS CLAMP

CROSS-REFERENCE TO RELATED APPLICATIONS

This application claims the benefit of U.S. Provisional Application No. 62/449,254, filed on Jan. 23, 2017, the disclosure of which is incorporated by reference in its entirety.

FIELD OF THE INVENTION

The invention relates generally to a nasal epistaxis clamp. More specifically, the present invention is related to a method and device for treating epistaxis using a novel nasal epistaxis clamp.

BACKGROUND

Epistaxis, bleeding from the nostril, nasal cavity, or nasopharynx, has been reported to occur in up to 60 percent of the general population. Nosebleeds are due to the bursting of a blood vessel within the nose and may be spontaneous or caused by trauma. The major blood arteries in the nasal cavity include the anterior and posterior ethmoid arteries and the sphenopalatine arteries. Approximately 5% to 10% of epistaxis is estimated to arise from the posterior nasal cavity, in an area known as Woodruff's plexus. Woodruff's plexus is located over the posterior middle turbinate and is primarily made up of connection of branches of the internal maxillary artery, namely, the posterior nasal, sphenopalatine, and ascending pharyngeal arteries. Posterior bleeds usually originate from the lateral wall and more rarely from the nasal septum.

Nosebleeds usually stop on their own, but in rare cases may lead to massive bleeding and even death. Nasal bleeding usually responds to simple first-aid measures such as compression. When epistaxis does not respond to simple treatment measures, the source of the bleeding must be located and treated appropriately. There is no single definitive treatment for the management of nose bleeds, and many factors, including severity of the bleeding, use of anticoagulants, and other medical conditions, may play a role in determining which treatment is utilized. Treatments to be considered may include topical vasoconstriction (i.e., pinching the nose over the fleshy portion), decongestant nasal sprays, chemical or electric cautery (i.e., burning the vessel shut), hemostatic agents (topical therapies to stop bleeding), nasal packing (nasal tampon or gauze impregnated with petroleum jelly), posterior gauze packing, use of a balloon system (including a modified Foley catheter), surgical arterial ligation (tying off the vessel), and embolization (a procedure to place material within the vessel to block it off). Referral to an otolaryngologist may be appropriate when bleeding is refractory, complications are present, or specialized treatment (balloon placement, arterial ligation, angiographic arterial embolization) is required.

Nosebleeds can be divided into 2 categories, based on the site of bleeding: anterior (in the front of the nose) or posterior (in the back of the nose), although most often, epistaxis originates in the anterior nasal cavity. Causes of epistaxis may be local (e.g., trauma, mucosal irritation, septal abnormality, inflammatory diseases, or tumors), systemic (e.g., blood disorders, arteriosclerosis, or hereditary hemorrhagic telangiectasia), or idiopathic (unknown). Local trauma is the most common, followed by facial trauma, foreign bodies, nasal or sinus infections, and prolonged inhalation of dry air. Tumors, vascular malformations, and septal perforations (holes in the nasal septum) are less common but may also result in epistaxis.

Trauma or injury to the turbinate mucosa and septum is a frequent cause of epistaxis. Nose picking and repeated irritation caused by the tips of nasal spray bottles commonly give rise to many anterior bleeds. Traumatic deformation and fractures of the nose and surrounding structures may also cause bleeding. Infections and mucosal inflammation, such as sinusitis, upper respiratory tract infections, and allergies can damage the respiratory lining to the point that it becomes irritated and bleeds. Additionally, septal deviations (bends in the wall that divides the nose between two sides), nasal fractures, and septal perforations (holes through the septum) can be a cause of irregular nasal airflow causing dryness and bleeding in some cases. Causes due to medical treatment, such as after endoscopic sinus surgery, skull base surgery, and orbital surgery may also be a cause of severe epistaxis.

While numerous nasal epistaxis devices are available in the art, many of these require insertion into the nasal cavity, which may worsen the bleeding or further irritate the nasal cavity. Other devices may be prone to slippage and may require repeated repositioning of the device. For example, exemplary nasal epistaxis devices are disclosed in U.S. Pat. Nos. 7,022,890; 7,108,706; and 7,695,490; and U.S. Pat. Publ. Nos. 2003/0105483; 2003/0236547; and 2016/0296378, the disclosures of which are incorporated herein by reference. The present invention therefore provides a simple and effective treatment for anterior epistaxis.

SUMMARY OF THE INVENTION

The present invention is directed to a nasal epistaxis claim. The invention provides a means for treatment of nasal bleeding. In certain embodiments, the nasal epistaxis device is particularly suited for control or treatment of bleeding originating from the anterior nasal cavity.

In one aspect, the invention provides a nasal epistaxis clamp, comprising: a solid plastic surface at one end, having an external linear ribbed surface; and expandable limbs at the opposite end, wherein the medial surface of each limb comprises a plurality of bubbles. In one embodiment, the overall length of the clamp is approximately 7 cm, and the overall width of the clamp is approximately 3 cm. In another embodiment, the solid plastic surface has a length of approximately 2.5 cm in length and a thickness of approximately 1 cm. In further embodiments, the expandable limbs each have a length of approximately 4.5 cm, or the expandable limbs are in contact with each other at the medial surface when not expanded. In still further embodiments, the solid plastic surface provides tension for the expandable limbs. In other embodiments, the expandable limbs exponentially increase the surface area of the external nasal surface for compression, or the expandable limbs expand to a width of approximately 3 cm, or the expanded width of approximately 3 cm fits over the external nasal surface at the base of the nostrils. In further embodiments, the plurality of bubbles of the medial surface of each expandable limb comprise plastic or rubber, or each bubble of the plurality of bubbles is approximately 3 mm in diameter and approximately 2 mm in height.

In another embodiment of the invention, the thickness of each limb is approximately 0.5 cm and is comprised of: 2 mm height of the bubbles; and 3 mm thickness of the limb. In still further embodiments, the expandable limbs provide sufficient compressive force to remain in place on the external nasal surface and to compress the nostrils to halt bleeding in the underlying tissue, or the bleeding originates in the anterior nasal cavity.

In another aspect, the invention provides a method for treating nasal bleeding, comprising the steps of: separating the expandable limbs of the nasal epistaxis clamp such that they are able to be placed on the external nostrils of a subject; placing the limbs on the external nostrils of the subject; and releasing the expandable limbs such that they compress the nasal surface of the subject.

In another aspect, the invention provides a nasal bleeding treatment kit comprising a nasal epistaxis clamp comprising: a solid plastic surface at one end, having an external linear ribbed surface; and expandable limbs at the opposite end, wherein the medial surface of each limb comprises a plurality of bubbles. In one embodiment, such a kit further comprises a package, said nasal epistaxis clamp being removably enclosed within said package.

These and other aspects, objects, features, and advantages of the example embodiments will become apparent to those having ordinary skill in the art upon consideration of the following detailed description of illustrated example embodiments.

DRAWING ELEMENTS

Figure 1:
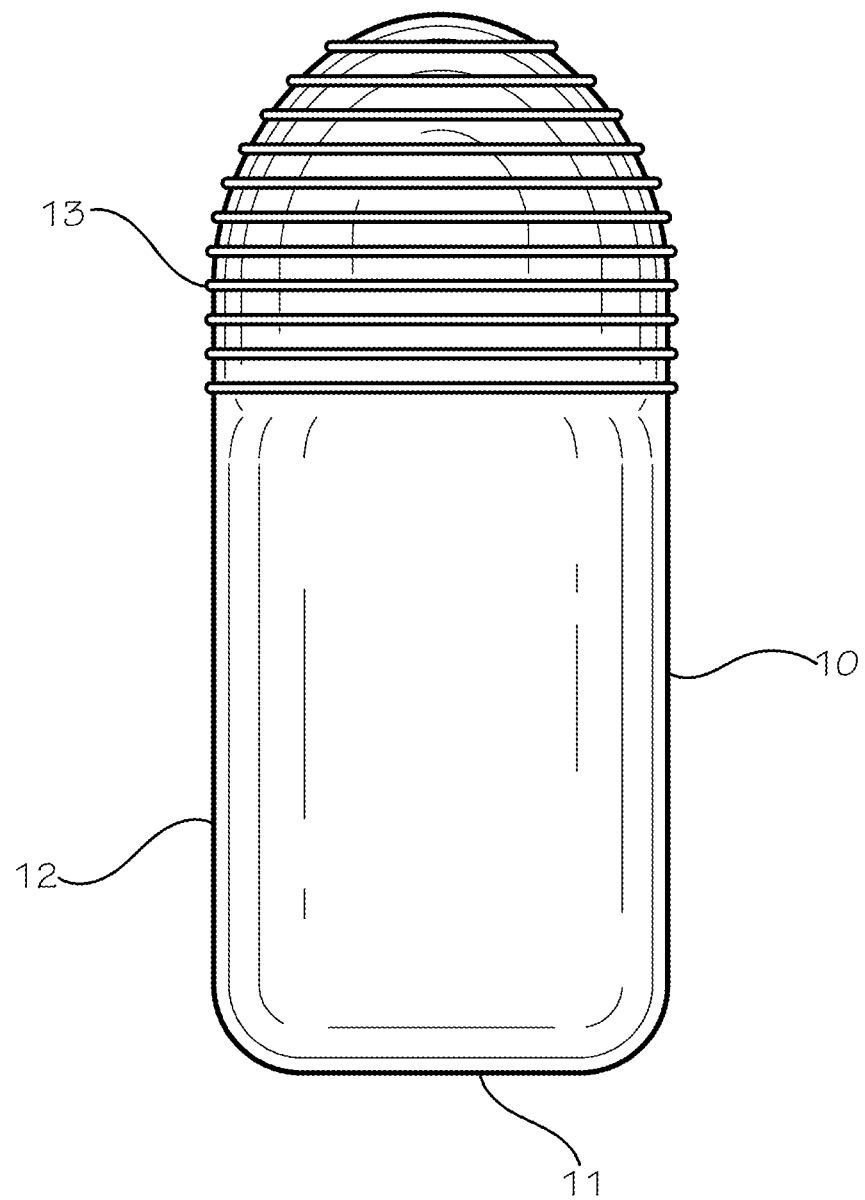
FIG. 1—Shows a frontal view of the nasal epistaxis device.

10 7 cm overall length of nasal epistaxis clamp
11 3 cm overall width of nasal epistaxis clamp
12 4.5 cm length of expandable limb
13 2.5 cm length of solid plastic ribbed surface
20 1 cm thickness of solid plastic ribbed surface
21 2.5 cm length of solid plastic ribbed surface
22 0.5 cm thickness of each limb, including 3 mm thickness of limb and 2 mm height of bubbles
23 7 cm overall length of nasal epistaxis clamp
24 4.5 cm length of expandable limb
25 2 mm height of bubbles
26 3 mm thickness of expandable limb
30 solid piece of plastic at upper end of nasal epistaxis clamp
31 plastic bubbles on interior, medial surface of each expandable limb
32 7 cm overall length of nasal epistaxis clamp
33 3 cm overall width of nasal epistaxis clamp

DETAILED DESCRIPTION OF THE INVENTION

The present invention can be understood more readily by reference to the following detailed description, examples, drawings, and claims, and their previous and following description. However, before the present devices, and methods are disclosed and described, it is to be understood that this invention is not limited to the specific devices and methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an," and "the" comprise plural referents unless the context clearly dictates otherwise. Ranges can be expressed herein as from "about" or "approximately" one particular value, and/or to "about" or "approximately" another particular value. When such a range is expressed, another aspect comprises from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

In simplest terms, disclosed herein is a nasal epistaxis clamp, a medical device that is used to compress the outer surface of a patient or subject's nostrils in which 90% of all nosebleeds occur. In general terms, the device comprises a solid plastic surface at one end, having an external linear ribbed surface; and expandable limbs at the opposite end, wherein the medial surface of each limb comprises a plurality of bubbles. In some embodiments, the bubbles are made of plastic or rubber. One of skill in the art will understand that a variety of materials may be used for the present device without deviating from the scope of the invention. The present device adds sufficient compressive force due to the expandable limbs or arms, and the unique compressive surface composed of separate, raised bubbles that dramatically increase the surface area of the compression surface, thereby increasing the amount of compression force to the underlying area of nasal bleeding. The device is specifically designed for nosebleeds originating from the anterior nasal cavity, where the vast majority of nosebleeds occur, providing temporary control of nasal bleeding. The bubble surface also provides a surer grip of the external nasal skin than a clamp composed of a smooth surface, which is prone to slippage.

In one aspect, the nasal epistaxis clamp disclosed herein has an overall length of about 7 cm and an overall width of about 3 cm. The limbs or arms are about 4.5 cm in length, with bubbles along the medial or contact surface of the limbs. The non-expandable head of the device is about 2.5 cm in length and about 1 cm in width and is composed of solid plastic measuring about 1 cm thick and about 3 cm wide, with an external linear ribbed surface. The solid plastic surface or end serves to provide tension for the expandable limbs, such that they remain in place and maintain compressive force when placed on the nasal surface. The device is applied to the nasal surface by separating the two limbs wide enough to fit on the external nasal surface of a patient or subject at the base of the nostrils, which is typically about 3 cm. When not expanded, the limbs are in contact with each other at the interior, or medial, surface. Due to the compressive force generated by the limbs, sufficient force is produced, both to stay in place on the external nasal surface, as well as to compress the nostrils to halt the underlying bleeding. In some embodiments, the limbs exponentially increase the surface area of the external nasal surface for compression. In this way, nasal bleeding may be treated more quickly in a patient or subject. The present invention also provides the steps for using the nasal epistaxis clamp.

Referring to FIG. 1, a view of one embodiment of the nasal epistaxis clamp is illustrated. Shown in frontal view, the nasal epistaxis device has an overall length 10 of about 7 cm, consisting of an upper, solid plastic ribbed surface 13, measuring about 2.5 cm in length, and a lower, expandable surface 12, measuring about 4.5 cm in length. The device has a width 11 of approximately 3 cm.

Figure 2:
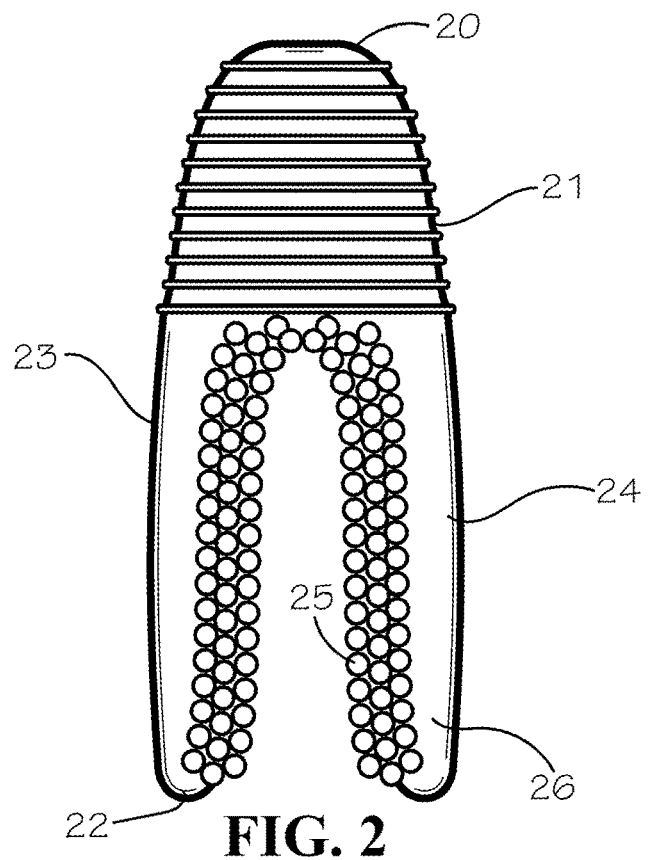
FIG. 2—Shows a side view of the device, depicting the top solid piece of plastic that provides tension for the lower separate arms for adequate compression, and the arms, which remain in contact with each other when not expanded. The bubbled surface of the interior of the arms expands exponentially the surface area that is available to compress the area of bleeding, where 90% of nosebleeds occur.

Referring to FIG. 2, a side view of one embodiment of the device is illustrated. Shown are the upper solid piece of plastic 21 measuring about 2.5 cm in length and having a thickness 20 of about 1 cm, and the lower expandable surface having 2 separate expandable limbs or arms 22, each having a thickness of approximately 0.5 cm, comprised of the 3 mm thickness of the limb 26 and the 2 mm height of the bubbles 25 on the inner, medial surface of each limb. The height of each bubble refers to the distance from the base of the bubble, where the bubble is joined to the limb or arm, to the outer surface, where the bubble contacts the nasal surface. Each limb or arm has a length 24 of approximately 4.5 cm. In some embodiments, each arm of the device is expandable up to about 1.5 cm, for a total maximal expansion of about 3 cm, the approximate thickness of the human nose.

Figure 3:
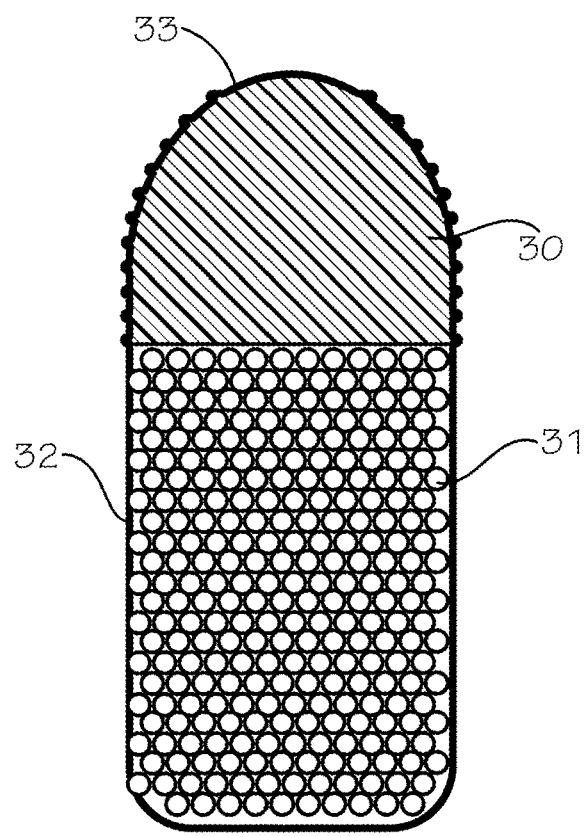
FIG. 3—Shows an inside view of one limb of the device. The inside of each limb is covered by bubbles measuring approximately 3 mm in diameter by 2 mm in height. The bubbles provide an expanded surface area for maximal contact of the external nose for maximum compression. The top of the device is a solid piece of plastic at the upper end that provides tension for lower limbs for compression. The limbs expand maximally to approximately 3 cm, corresponding to the average width of the human nose at the base of the nostrils.

Referring to FIG. 3, the inside view of one arm of the device is illustrated. Shown is the interior or medial surface, which has an overall length 32 of about 7 cm and a width 33 of about 3 cm, and is made up of a plurality of bubbles 31, each measuring approximately 3 mm in diameter by 2 mm in height. These bubbles provide an expanded surface area for maximal contact of the external nose for maximum compression.

The nasal epistaxis device disclosed herein may many uses known to those of skill in the art. For example, the disclosed device can be used for treatment of nasal epistaxis or nosebleed, particularly originating from the anterior nasal cavity. However, as would be understood by one of skill in the art, any nasal bleeding requiring compression of the external nasal tissues may be treated with the present device. In some embodiments, the present device is designed for use by medical personnel, in a clinical or hospital setting. In other embodiments, the present device is designed for personal use, for example for use at home without the need for medical personnel.

The invention also provides a method for treating nasal bleeding, comprising the steps of: separating the expandable limbs of the nasal epistaxis clamp such that they are able to be placed on the external nostrils of a subject; placing the limbs on the external nostrils of the subject; and releasing the expandable limbs such that they compress the nasal surface of the subject. Also provided are kits comprising the device. Such a kit may comprise the device as described herein, and may further comprise the device removably enclosed within a package, along with instructions for use and/or cleaning or sterilizing as appropriate. With the device, methods, and kits as described herein, the external nasal tissues are compressed such that the underlying bleeding in the nasal cavity may be halted. Once the device is removed, it may be repositioned on the nasal tissues as necessary on subsequent occasions with no reduction in the device's function. As would be understood by one of skill in the art, the present device may be appropriate for reuse as needed. The present device may be used for multiple patients or subjects as needed, following appropriate cleaning and/or sterilization procedures known in the art.

As can be easily understood from the foregoing, the basic concepts of the present invention may be embodied in a variety of ways. The invention involves numerous and varied embodiments of a nasal epistaxis clamp and methods of using same. While the present invention has been described with respect to the preferred embodiments thereof, it will be recognized by those of ordinary skill in the art that many changes and modifications may be made without departing from the spirit and scope of the invention.

Other aspects of the invention will be apparent to those skilled in the art from consideration of the specification and practice of the invention disclosed herein. It is intended that the specification and examples be considered as exemplary only, with a true scope and spirit of the invention being indicated by the following claims.

As such, the particular embodiments or elements of the invention disclosed by the description or shown in the figures accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Thus, the Applicant should be understood to claim at least: (i) the nasal epistaxis clamp herein disclosed and described, (ii) the related methods disclosed and described, (iii) similar, equivalent, and even implicit variations of each of these devices and methods, (iv) those alternative embodiments which accomplish each of the functions shown, disclosed, or described, (v) those alternative designs and methods which accomplish each of the functions shown as are implicit to accomplish that which is disclosed and described, (vi) each feature, component, and step shown as separate and independent inventions, (vii) the applications enhanced by the various systems or components disclosed, (viii) methods and apparatuses substantially as described herein and with reference to any of the accompanying examples, and (ix) the various combinations and permutations of each of the previous elements disclosed.

The claims set forth in this specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent non-provisional, continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent non-provisional continuation, division, or continuation-in-part application thereof or any reissue or extension thereon.

The claims set forth below are intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any non-provisional, continuation, division, or continuation-in-part, or similar application.

What is claimed is:

1. A nasal epistaxis clamp, comprising:
   a solid plastic surface at a first end, having an external linear ribbed surface; and
   expandable limbs at a second end opposite the first end, each of the expandable limbs having a medial surface comprising a plurality of bubbles, wherein the plurality of bubbles is configured to contact the external nasal surfaces of a subject.

2. The nasal epistaxis clamp of claim 1, wherein the overall length of the clamp is approximately 7 cm, and the overall width of the clamp is approximately 3 cm.

3. The nasal epistaxis clamp of claim 1, wherein the solid plastic surface has a length of approximately 2.5 cm in length and a thickness of approximately 1 cm.

4. The nasal epistaxis clamp of claim 1, wherein the expandable limbs each have a length of approximately 4.5 cm.

5. The nasal epistaxis clamp of claim 4, wherein the expandable limbs are in contact with each other at the medial surface when not expanded.

6. The nasal epistaxis clamp of claim 1, wherein the solid plastic surface provides tension for the expandable limbs.

7. The nasal epistaxis clamp of claim 1, wherein the expandable limbs exponentially increase the surface area of the external nasal surface for compression.

8. The nasal epistaxis clamp of claim 1, wherein the expandable limbs expand to a width of approximately 3 cm.

9. The nasal epistaxis clamp of claim 8, wherein the expanded width of approximately 3 cm fits over the external nasal surface at the base of the nostrils.

10. The nasal epistaxis clamp of claim 1, wherein the plurality of bubbles of the medial surface of each expandable limb comprises plastic or rubber.

11. The nasal epistaxis clamp of claim 10, wherein each bubble of the plurality of bubbles is approximately 3 mm in diameter and approximately 2 mm in height.

12. The nasal epistaxis clamp of claim 1, wherein the thickness of each limb is approximately 0.5 cm and is comprised of:
    2 mm height of the bubbles; and
    3 mm thickness of the limb.

13. The nasal epistaxis clamp of claim 1, wherein the expandable limbs provide sufficient compressive force to remain in place on the external nasal surface and to compress the nostrils to halt bleeding in the underlying tissue.

14. The nasal epistaxis clamp of claim 13, wherein the bleeding originates in the anterior nasal cavity.

15. A method for treating nasal bleeding, comprising the steps of:
    separating expandable limbs of a nasal epistaxis clamp such that they are positionable on the external nasal surfaces of a subject, each expandable limb having a medial surface comprising a plurality of bubbles;
    positioning the limbs on the external nasal surfaces of the subject, such that the bubbles of the outer surface contact the external nasal surfaces of the subject; and
    releasing the expandable limbs such that they apply a compressive force to the external nasal surfaces of the subject.

16. A nasal bleeding treatment kit comprising a nasal epistaxis clamp, comprising:
    a solid plastic surface at a first end, having an external linear ribbed surface; and
    expandable limbs at a second end opposite the first end, each of the expandable limbs having a medial surface comprising a plurality of bubbles, wherein the plurality of bubbles is configured to contact the external nasal surfaces of a subject.

17. The nasal bleeding treatment kit of claim 16, further comprising a package, said nasal epistaxis clamp being removably enclosed within said package.

* * * * *